United States Patent [19]

Winkley et al.

[11] Patent Number: 4,785,118
[45] Date of Patent: * Nov. 15, 1988

[54] PROCESS FOR PREPARING INDOLINE-2-CARBOXYLIC ACIDS VIA ALPHA-HYDROXY-2-NITROBENZENE-PROPANOIC ACID

[75] Inventors: Michael W. Winkley; Ronald J. McCaully, both of Malvern, Pa.

[73] Assignee: American Home Products Corporation, New York, N.Y.

[*] Notice: The portion of the term of this patent subsequent to Sep. 30, 2003 has been disclaimed.

[21] Appl. No.: 925,573

[22] Filed: Oct. 31, 1986

Related U.S. Application Data

[60] Division of Ser. No. 829,674, Feb. 14, 1986, Pat. No. 4,645,857, which is a division of Ser. No. 700,371, Feb. 11, 1985, Pat. No. 4,585,879, which is a continuation of Ser. No. 565,083, Dec. 23, 1983, abandoned.

[51] Int. Cl.$^4$ ............................................ C07D 209/42
[52] U.S. Cl. .................................................... 548/491
[58] Field of Search ......................................... 548/491

[56] References Cited

U.S. PATENT DOCUMENTS 4,060,626 11/1977 Hrstka et al. ...................... 424/274
4,614,806 9/1986 Buzby, Jr. et al. .................. 562/434

FOREIGN PATENT DOCUMENTS 2085880 5/1982 United Kingdom .

OTHER PUBLICATIONS

Houlihan, ed., The Chemistry of Heterocyclic Compounds, vol. 25, part 1, pp. 369–399, (Wiley Interscience, New York, 1972).
Hudson, C. B. and Robertson, A. V., Australian Journal of Chemistry, 20, 1935–41, (1967).
Stanton et al., Journal of Medicinal Chemistry, 26, 1267–77, 1268, (1983).
Corey et al., Journal of the American Chemistry Society, 2476–2488, at 2480, (1970).
Malinowski, Roczniki Chemii, 26, 85, (1952), English abstract.
Hepburn et al., Chem. Abstracts, 82:3698n, (1975).

Primary Examiner—Mary E. Ceperley
Attorney, Agent, or Firm—Arthur G. Seifert

[57] ABSTRACT

Disclosed herein is a process for obtaining indoline-2-carboxylic acid (or derivatives thereof) comprising the following steps: (a) reducing α-oxo-2-nitrobenzenepropanoic acid to α-hydroxy-2-nitrobenzenepropanoic acid, (b) replacing the hydroxyl group of the latter with a chlorine atom utilizing a selected Vilsmeier chlorinating reagent at temperatures of at least 20° C., (c) reducing the nitro group of the resulting α-chloro-2-nitrobenzenepropanoic acid to obtain α-chloro-2-aminobenzenepropanoic acid, and (d) cyclizing the latter in aqueous base to form the desired indoline-2-carboxylic acid. Alternately, steps (c) and (d) may be combined in a one pot step by using, for example, a Raney nickel-hydrazine reducing medium.

3 Claims, No Drawings

PROCESS FOR PREPARING INDOLINE-2-CARBOXYLIC ACIDS VIA ALPHA-HYDROXY-2-NITROBENZENE-PROPANOIC ACID

This application is a division of application Ser. No. 829,674, filed on Feb. 14, 1986 now U.S. Pat. No. 4,645,857 which is a division of application Ser. No. 700,371 filed on Feb. 11, 1985 now U.S. Pat. No. 4,585,879 which is a continuation of application Ser. No. 565,083, filed Dec. 23, 1983 now abandoned.

This invention describes a process for making indoline-2-carboxylic acids of the formula

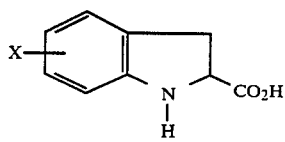
I wherein X is hydrogen, chlorine, bromine, $C_{1-4}$ alkyl or $C_{1-4}$ alkoxy.

The overall process is shown in the following diagram:

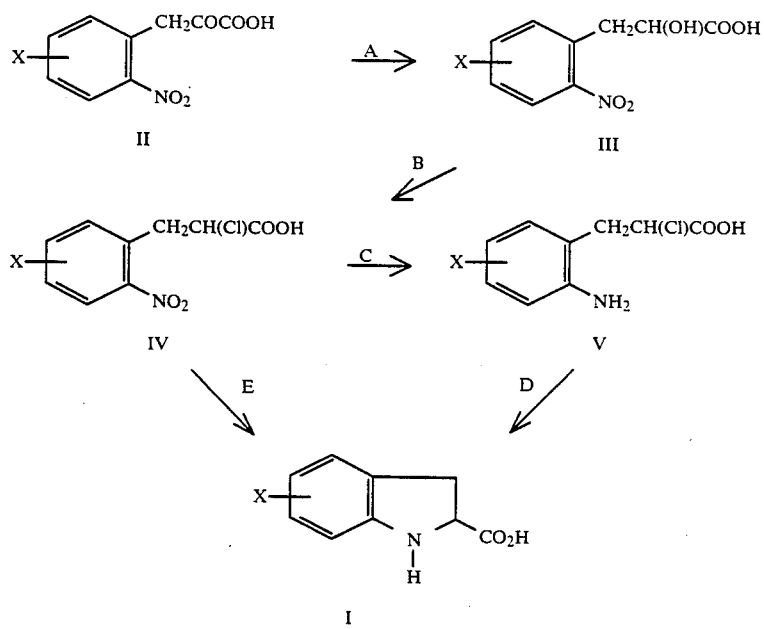

Steps B, D and E in this process are also novel and patent protection is sought for them as well as for the overall process. In addition, the intermediate 2-amino-α-chlorobenzenepropanoic acids (V) are novel and patent protection is likewise sought for these compounds.

BACKGROUND OF THE INVENTION

Indoline-2-carboxylic acids have heretofore been prepared by first forming the corresponding indole-2-carboxylic acid and then reducing the 2,3-double bond. The chief drawback in such preparations has been the lack of a satisfactory process for reducing the 2,3-double bond.

One of the methods of obtaining the indole-2-carboxylic acid to be reduced has been via the Reissert synthesis wherein o-nitrophenylpyruvic acid (II above where X is hydrogen) is reductively cyclized directly to the indoline-2-carboxylic acid using zinc and acetic acid or ferrous sulfate and ammonium hydroxide. See Weissberger, ed., *The Chemistry of Heterocyclic Compounds*, Vol. 25, part 1, pp. 396-399 (Wiley Interscience, New York, 1972).

Three methods are reported for reducing indole-2-carboxylic acid to indoline-2-carboxylic acid. Hudson and Robertson, Australian Journal of Chemistry, 20, 1935-41 (1967), first converted the acid to the amide and reduced the 2,3-double bond of the amide using phosphonium iodide/hydriodic acid. They then converted the resulting indoline-2-carboxamide to the desired indoline-2-carboxylic acid by hydrolysis. Y. Omote et al., Nippon Kagaku Zasshi, 87, 760 (1966), also reported an indirect reduction. [See Stanton et al., Journal of Medicinal Chemistry, 26, 1267-77 at 1268 (1983)]. In this method the indole-2-carboxylic acid was first converted to the N-acetyl derivative which was reduced by hydrogenation at atmospheric pressure in the presence of platinum oxide. The resulting N-acetyl-indoline-2-carboxylic acid was then hydrolized to remove the acetyl group. Corey et al., Journal of the American Chemical Society, 92, 2476-2488, at 2480 (1970), directly reduced indole-2-carboxylic acid ethyl ester using excess dry hydrogen chloride gas and tin and absolute ethanol in a sealed bomb.

Applicants' new process for producing indoline-2-carboxylic acids avoids these indirect and inefficient reductions by cyclization of their new intermediate α-chloro-2-aminobenzenepropanoic acids V to yield the desired indoline-2-carboxylic acids directly.

The indoline-2-carboxylic acids of Formula I are useful as starting materials for the preparation of N-(3-mercapto-2-alkyl-1-oxopropyl)-indoline-2-carboxylic acids and N-(2-substituted-1-oxoalkyl)-indoline-2-carboxylic acids thereof which have antihypertensive and angiotensin converting enzyme (ACE) inhibitory properties. These antihypertensive agents and ACE inhibitors are disclosed, respectively, in U.S. Pat. No.

4,303,583, issued on Dec. 1, 1981, to D. H. Kim and R. J. McCaully and in U.S. Pat. No. 4,350,633, issued on Sept. 21, 1982, also to D. H. Kim and R. J. McCaully.

DETAILED DESCRIPTION OF THE INVENTION

In step A of Applicants' process, commercially available α-oxo-2-nitrobenzenepropanoic acid [i.e. o-nitrophenylpyruvic acid] (II) is selectively reduced to give α-hydroxy-2-nitrobenzenepropanoic acid (III). Good yields are obtained in this selective reduction using sodium borohydride as the reducing agent in a hydroxylic solvent, such as ethanol or water.

In step B, the resulting α-hydroxy-2-nitrobenzenepropanoic acid (III) is reacted with a Vilsmeier chlorinating reagent in order to form an α-chloro-2-nitrobenzenepropanoic acid (IV) by replacement of the hydroxyl group with a chlorine atom. The Vilsmeier chlorinating reagent is formed from the combination of a chlorinating agent and an amide of the formula $R_2CONR_1R_1$, where $R_1$ and $R_2$ are preferably a methyl or ethyl group. A suitable chlorinating agent may be selected from thionyl chloride, oxalyl chloride, phosphorus oxychloride, phosphorus pentachloride, and sulfuryl chloride, with thionyl chloride being especially preferred. A suitable amide may be selected from N,N-dimethylformamide, N,N-diethylformamide, N,N-dimethylacetamide, or N,N-diethylacetamide, with N,N-dimethylformamide (DMF) being especially preferred. The Vilsmeier reagent may be formed separately and then added to the α-hydroxy-2-nitrobenzenepropanoic acid substrate, or the Vilsmeier reagent may be formed in situ, usually by combining the substrate and the amide first and then adding the chlorinating agent.

In order to ensure chlorination at both the hydroxy and acyl sites of the substrate, thereby avoiding intermolecular condensation, the amide portion of the Vilsmeier reagent is preferably present in 2–6 moles per mole of substrate. Good yields are obtained with 2–3 moles of amide per mole of substrate. For the same reason, the chlorinating agent should be present in at least 2 moles per mole of substrate. Preferably the chlorinating agent is present in excess of 4 moles per mole of substrate and may be present in up to 34 moles per mole of substrate. Such large excesses are used particularly when no inert solvent is used for the reaction.

Accordingly, the reaction of step B can be run without a solvent or with an inert organic solvent such as dichloromethane, dichloroethane, chloroform, methylene chloride or ethylene chloride. Dichloromethane is the preferred solvent. Additionally, temperatures above 20° C. are necessary when reaction B is in progress. Preferably, the reaction temperature is at least 25° C. and may vary up to about 50° C. depending upon the particular Vilsmeier reagent and solvent used. A prefered temperature range is 25°–35° C., and, at such temperatures, a reaction time of 12–24 hours is preferred. Conveniently, an overnight reaction of about 18 hours at room temperatures of 25° C. is used.

The product IV, in which X is H [lit., S. Malinowski, Roczniki Chemii, 26, 85 (1952)] initially isolated by preparative HPLC as the free acid. Later it was more conveniently isolated directly from the crude reaction mixture as the 2,6-dimethylpiperidine salt.

The nitro group of this α-chloro-2-nitrobenzenepropanoic acid IV may be reduced by various reducing agents. Conveniently, it was reduced with hydrogen over palladium on carbon in methanol at ambient temperature and pressure to give α-chloro-2-aminobenzene-propanoic acid (V).

The α-chloro-2-nitrobenzenepropanoic acid (V) or its amine salt is next reduced in a basic medium to afford either the intermediate α-chloro-2-aminobenzenepropanoic acid (V) or the desired indoline-2-carboxylic acid (I). The reduction may be done catalytically in the presence of standard hydrogenation catalysts such as palladium on carbon in a hydrogen atmosphere, in which case the intermediate (V) is obtained. Alternatively, the reduction can be carried out with reducing agents that are compatible with a basic reaction medium, such as Raney nickel-hydrazine, in which case the desired indoline-2-carboxylic acid (1a) is obtained directly. In this case, reactions (steps) C and D are combined in that they take place consecutively in the same reaction vessel. The work up steps of separating and isolating the α-chloro-2-aminobenzenepropanoic acid V are therefor avoided.

In those instances in which the intermediate (V) is generated and isolation is preferred, it is most convenient to isolate the compound as a salt formed with an alicyclic or cyclic amine. 2,6-Dimethylpiperidine is the preferred amine. Conversion of (V) to the indoline-2-carboxylic acid (I) is achieved by contacting a dispersion of (V) in a hydroxylic solvent with an alkaline metal hydroxide. Isolation of the product follows standard procedures.

X, as defined herein, may also include fluorine and "halogen" refers to fluorine, chlorine and bromine.

The following examples further illustrate the means and best mode for carrying out the above-described invention.

EXAMPLE 1

α-Hydroxy-2-Nitrobenzenepropanoic Acid

A. To a magnetically stirred solution of α-oxo-2-nitrobenzenepropanoic acid (40.00 g) in absolute ethanol (500 ml) cooled in ice water was added sodium borohydride (20.0 g) in portions at such a rate as to maintain the temperature between 25 and 30°. The temperature of the solution was maintained between 25°–30° for a further 4 hours after the addition. The solution was evaporated to near dryness, and the residue was dissolved in water. The solution was acidified with concentrated hydrochloric acid and extracted four times with ethyl acetate. The organic extract was washed twice with water and dried over magnesium sulfate. Evaporation gave a syrup which was crystallized (seeding) from dichloromethane-cyclohexane; yield 28.26 g (70%), m.p. 87–90°. Recrystallization with decolorization from water gave 20.31 g (50%) of the titled compound; m.p. 104°–105°; MH+ 212 (CI mode), $\lambda_{max}^{KBr}$ 1715 (COOH), 3445 (OH) cm$^{-1}$; pmr (CDCl$_3$, DMSO-d$_6$) δ3.04–3.72 (8 lines, AB part of an ABX system, —CH$_2$—), 4.34–4.54 (q centered at 4.45, width 12 Hz, symmetrically spaced, X part of ABX system, —C$\underline{H}$(OH)), 7.28–7.68 (m, 3 aromatic protons and exchangeable O$\underline{H}$), 7.80–8.00 ("d" centered at 7.95, "J" 8 Hz, 1 aromatic proton).

Analysis for: C$_9$H$_9$NO$_5$: Calculated: C, 51.19; H, 4.30; H, 6.63. Found: C, 51.53; H, 4.39; N, 6.28.

B. Alternatively, the preceding compound was prepared as follows:

To a magnetically stirred suspension of α-oxo-2-nitrobenzenepropanoic acid (5.00 g) in water (75 ml)

containing 1 drop of decyl alcohol was added sodium borohydride (2.50 g) in portions to maintain a temperature between 45 and 50°. The resulting solution was then left at room temperature for 2½ hours. The solution was acidified with concentrated hydrochloric acid and seeded. Stirring and cooling gave crude product; yield 5.01 g, m.p. 84°–90°. Recrystallization from water gave titled product; yield 2.63 g (52%), m.p. 95°–98° with spectral data as above.

Analysis for: $C_9H_9NO_5$: Calculated: C, 51.19; H, 4.30; H, 6.63. Found: C, 50.77; H, 4.24; N, 6.28.

EXAMPLE 2

α-Chloro-2-Nitrobenzenepropanoic Acid

To a magnetically stirred solution of α-hydroxy-2-nitrobenzenepropanoic acid (1.00 g, 4.74 mmol) in N,N-dimethylformamide (2 ml, 25.85 mmol) cooled in ice was added thionyl chloride (12 ml, 164.5 mmol) slowly dropwise. The cooling bath was removed and the solution was left at room temperature (20° C.) overnight. The solution was evaporated to a solid. Ice and dichloromethane were added and the mixture was stirred magnetically for one hour, during which time it warmed to room temperature. The layers were separated and the organic phase was washed six times with water. The dried (MgSO$_4$) solution was evaporated to a syrup which was subjected to an oil pump vacuum; yield 1.09 g Examination of the syrup on the μ-Bondapak $C^{18}$ chromatographic column (Waters Associates) using a solvent system containing 90% of 0.1N ammonium acetate, pH 4.0 buffer and 10% acetonitrile revealed three components. The major component, which was present to the extent of 74% of the mixture, was separated on a Waters Associates Prep. 500 unit using a $C^{18}$ cartridge and the solvent system mentioned above. Appropriate fractions were evaporated to a syrup below room temperature. The syrup was mixed with dilute hydrochloric acid and chloroform. The organic phase was washed twice with saturated brine and dried (MgSO$_4$). The solution was evaporated to a syrup which crystallized spontaneously (0.48 g, 44%). Crystallization from chloroform-cyclohexane gave 0.33 g (31%) of the titled product; m.p. 108°–109°; MH+ 230 (1 Cl, CI mode); $\lambda_{max}^{KBr}$ 1707, 1725 (COOH), pmr (CDCl$_3$) δ3.22–3.96 (8 lines, AB part of an ABX system, —CH$_2$—), 4.60–4.88 (q centered at 4.76, width 14 Hz, "J" 6 Hz, X part of ABX system, >C$\underline{H}$Cl), 7.32–8.16 (m, aromatic).

Analysis for: $C_9H_8NClO_4$: Calculated: C, 47.08; H, 3.51; Cl, 15.44; N, 6.10. Found: C, 47.14; H, 3.62; Cl, 15.20; N, 6.23.

S. Malinowski [Rocziniki Chemii 26, 85 (1952)] reported m.p. 109°–110° for the acid. It was found that the acid formed a crystalline 2,6-dimethylpiperidine salt, m.p. 139°–141° (from ether), which was utilized to isolate the titled acid as described below in Example 3.

EXAMPLE 3

α-Chloro-2-Nitrobenzenepropanoic Acid, 2,6-Dimethylpiperidine Salt

To magnetically stirred N,N-dimethylformamide (6 ml, 77.6 mmol) cooled in ice was added thionyl chloride (36 ml, 493.5 mmol) slowly dropwise to generate the Vilsmeier reagent. To the cold reagent was added portionwise α-hydroxy-2-nitrobenzenepropanoic acid (3.00 g, 14.2 mmol). The solution was left at ice bath temperature for half an hour and then left at room temperature (about 20° C.) for 40 hours. The solution was evaporated and the resulting solid was dissolved in dichloromethane. The solution was added cautiously to stirred ice and the mixture was stirred for one hour, during which time it warmed to room temperature. The organic layer was washed with water (×3), dried over magnesium sulfate and evaporated to a syrup which was subject to an oil pump vacuum; yield 3.78 g. The syrup was dissolved in ether (50 ml) and 2,6-dimethylpiperidine was added to neutrality (pH paper). Seeding with the titled salt (prepared above from pure α-chloro-2-nitrobenzenepropanoic acid) and scratching followed by magnetic stirring gave 2.58 g (53%) of crude titled product, m.p. 134°–137°. The product was dissolved in methanol and the solution was decolorized. Evaporation gave a syrup which was crystallized by warming in ether, followed by refrigeration; yield 2.20 g; m.p. 139°–140°, MH+ 230 (1 Cl, C.I. mode); $\lambda_{max}^{KBR}$ 1590, 1520 cm$^{-1}$; pmr (DMSO-d$_6$) δ1.17 (d, J$_{Me,H}$ 6 Hz, Me), 1.24–1.84 (m, —CH$_2$CH$_2$CH$_2$—), 2.76–3.16 (bm, C$\underline{H}$—NH—C$\underline{H}$), 3.12–3.70 (8 lines AB part of an ABX system, —C$\underline{H_2}$—CHCl), 4.16–4.36 (q centered at 4.27, width 14 Hz, "J" 6 Hz, X part of an ABX system, —C$\underline{H}$Cl—), 7.38–7.76 (m, aromatic) 7.80–7.98 ("d" centered at 7.91; "J" 8 Hz, 1 aromatic proton).

Analysis for: $C_9H_8ClNO_4 \cdot C_7H_{15}N$: Calculated: C, 56.06; H, 6.76; Cl, 10.34; N, 8.17. Found: C, 56.09; H, 6.75; Cl, 9.95; N, 7.81.

EXAMPLE 4

α-Chloro-2-aminobenzenepropanoic Acid, 2,6-dimethylpiperidine Salt

α-Chloro-2-nitrobenzenepropanoic acid, 2,6-dimethylpiperidine salt (1.37 g) was hydrogenated in methanol (100 ml) over 5% palladium on carbon (0.16 g) at ambient temperature and pressure. After the theoretical uptake of hydrogen had been achieved the reaction was stopped and the catalyst removed by filtration through analytical filter aid. The solution was evaporation below room temperature to a syrup which was co-evaporated with cyclohexane. The resulting syrup was seeded and stirred magnetically in ether. The reulting crystalline product was collected and washed with ether; yield 1.09 g (87%); mp 120–122°; MH+—H$_2$O, 182 (1 Cl, CI mode); $\lambda_{max}^{KBr}$ 3240, 3343, 3404 (NH), 1627, 1579 cm$^{-1}$; pmr (DMSO-d$_6$) δ1.18 (d, J$_{Me,H}$6Hz, Me), 1.26–1.84 (m, —C$_2$CH$_2$CH$_2$—), 2.66–3.36 (8 lines, AB part of an ABX system, —CH2—CHCl), 2.78–3.14 (bm overlapping ABX pattern, C$\underline{H}$-NH-CH), 4.12–4.30 (t centered at 4.21, width 14 Hz, "J" 7 Hz, X part of ABX system, >C$\underline{H}$Cl), 7.38–7.70 (m, 2 aromatic protons), 7.78–8.08 (m, 2 aromatic protons).

Analysis for: $C_9H_{10}ClNO_2 \cdot C_7H_{15}N$: Calculated: C, 61.43; H, 8.05; Cl, 11.33; N, 8.95: Found: C, 61.36; H, 7.82; Cl, 11.43; N, 9.20

EXAMPLE 5

2,3-Dihydro-1H-indole-2-caraboxylic Acid

To 1 ml N sodium hydroxide and water (3 ml) under nitrogen at room temperature was added α-chloro-2-aminobenzenepropanoic acid, 2,6-dimethylpiperidine salt (0.6257 g). After 15 minutes a further 1 ml of N sodium hydroxide was added and the solution was kept under nitrogen at room temperature overnight. The solution was filtered and evaporated to slightly smaller volume. The solution was stirred magnetically, and the pH of the solution was adjusted to a value of 3 by the dropwise addition of dilute hydrochloric acid. The product crystallized readily. After refrigeration the product was collected and washed twice with small volumes of ice cold water. The product was dried at room temperature in a vacuum over phosphorus pentoxide to give hydrated titled compound; yield 0.233 g (71%); mp 154°–156°; MH+ 164 (CI mode); $\lambda_{max}^{KBr}$ 1615, 1580 cm$^{-1}$; pmr (DMSO-d$_6$); δ3.90–4.46 (7 lines, AB part of an ABX system, —C$\underline{H}_2$—), 4.16–4.38 (q centered at 4.27, width 16 Hz, "J" 6 Hz, X part of ABX system, >C$\underline{H}$CO$_2$H), 4.00–6.40 (bs NH$_2$+), 6.44–6.68 (m, 2 aromatic protons) 6.80–7.10 (m, 2 aromatic protons).

Analysis for: C$_9$H$_9$NO$_2$·0.1H$_2$O: Calculated: C, 65.52; H, 5.62; N, 8.49. Found: C, 65.42; H, 5.80; N, 8.30.

The spectral data of the compound were identical with those of material prepared by previous methods.

EXAMPLE 6

α-Chloro-2-nitrobenzenepropanoic acid, 1-dimethylethyl ester

To magnetically stirred N,N-dimethylformamide (12 ml, 155.1 mmol) cooled in ice was added thionyl chloride (72 ml, 987.1 mmol) slowly dropwise to generate the Vilsmeier reagent. To the cold reagent was added portionwise α-hydroxy-2-nitrobenzenepropanoic acid (6.0 g, 28.4 mmol). The solution was left for half an hour at ice bath temperature and then left at room temperature overnight. Evaporation gave a solid which was subjected to an oil pump vacuum. The residue was dissolved in dichloromethane and added dropwise to t-butanol (150 ml) at ambient temperature. The resulting solution, protected from moisture, was left overnight at room temperature. The solution was evaporated to an oil which was subjected to an oil pump vacuum. The resulting oil was dissolved in chloroform and applied to a column (50×3.8 cm) of silica gel (J. T. Baker) prepacked in chloroform. Elution was with chloroform and the fractionation was monitored by tlc on silica gel GF (Analtech) with chloroform as developer. Evaporation of appropriate fractions gave a major component (4.61 g of yellow oil) slightly contaminated with a slower component. The oil was dissolved in chloroform and applied to a second column (52×3.2 cm) of silica gel prepacked in chloroform. Elution with chloroform gave fractions containing the major component freed from its contaminant. Evaporation to smaller volume followed by decolorization and solvent removal gave titled compound as a yellow oil; yield 3.17 g (39%); MH+ 286 (1Cl, CI mode); $\lambda_{max}^{KBr}$ 1730 cm$^{-1}$ (ester); pmr (CDCl$_3$) δ1.45 (s, t-Bu), 3.28–3.82 (8 lines, AB part of an ABX system, —C$\underline{H}_2$—CHCl—), 4.42–4.68 (q centered at 4.57, width 14 Hz, X part of ABX system, "J" 6 Hz, >C$\underline{H}$(Cl)—), 7.38–7.70 (m, 3 aromatic protons), 7.98–8.12 (m, 1 aromatic proton).

Analysis for: C$_{13}$H$_{16}$ClNO$_4$: Calculated: C, 54.65; H, 5.64; Cl, 12.41; N, 4.90. Found: C, 53.89; H, 5.53; Cl, 12.28; N, 4.86.

Crystalline α-chloro-2-nitrobenzenepropanoic acid, 1-dimethylethyl ester

Chromatographically purified, syrupy, α-chloro-2-nitrobenzenepropanoic acid, 1-dimethylethyl ester, protected from light, crystallized on long standing at room temperature. Trituration with heptane gave crystalline material, mp 53°–55° C. Recrystallization of 2.21 g of this material from heptane gave 1.92 g of product, mp 54°–56° C. Spectral data were as recorded previously.

Analysis for: C$_{13}$H$_{16}$ClNO$_4$: Calculated: C, 54.65; H, 5.64; Cl, 12.41; N, 4.90. Found: C, 54.75; H, 5.60; Cl, 12.28; N, 5.09.

EXAMPLE 7

α-Chloro-2-Nitrobenzenepropanoic Acid, 2,6-Dimethylpiperidine Salt

To N,N-dimethylformamide (12 ml, 155.1 mmol) cooled in ice was added thionyl chloride (72 ml, 987.1 mmol) slowly dropwise. α-Hydroxy-2-nitrobenzenepropanoic acid (6.00 g, 28.4 mmol) was added to the cold solution and the resulting yellow solution was kept at ice bath temperature for half an hour and then left at room temperature (25° or more) overnight. The solution was evaporated to a syrup which was dissolved in dichloromethane. The solution was added cautiously to stirred ice. The mixture was stirred for 1 hour during which time the mixture was allowed to warm to room temperature. The organic extract was washed (×4) with water, dried over magnesium sulfate and evaporated to a syrup which was subjected to an oil pump vacuum; yield=8.71 g. To the syrup dissolved in ether (40 ml) was added 2,6-dimethylpiperidine until the solution was neutral (pH paper). Seeding and stirring gave 8.00 g of titled product (82%); mp=139°–140°, MH+ 230 (1 Cl, C.I. mode); $\lambda_{max}^{KBr}$ 1590, 1520 cm$^{-1}$; pmr (DMSO-d$_6$) δ1.17 (d, J$_{Me, H}$ 6 Hz, Me) 1.24–1.84 (m, —CH$_2$CH$_2$CH$_2$—), 2.76–3.16 (bm, C$\underline{H}$—NH—C$\underline{H}$) 3.12–3.70 (8 lines, AB part of an ABX system —C$\underline{H}_2$CHCl), 4.16–4.36 (q centered at 4.27, width 14 Hz, "J" 6 Hz, X part of an ABX system —C$\underline{H}$Cl—), 7.38–7.76 (m, aromatic) 7.80–7.98 ("D" centered at 7.91, "J" 8 Hz, 1 aromatic proton).

Analysis for: C$_9$H$_8$ClNO$_4$·C$_7$H$_{15}$N: Calculated: C, 56.06; H, 6.76; N, 8.17; Cl, 10.34. Found: C, 56.16; H, 6.65; N, 8.11; Cl, 9.95.

EXAMPLE 8

α-Chloro-2-nitrobenzenepropanoic acid 2,6-dimethylpiperidine salt

To magnetically stirred N,N-dimethylformamide (2 ml, 25.8 mmol) cooled in ice was added slowly dropwise thionyl chloride (3 ml, 41.1 mmol), and the resulting cold Vilsmeier reagent was diluted with dichloromethane (10 ml). α-Hydroxy-2-nitrobenzenepropanoic acid (2.00 g, 9.47 mmol), followed by an additional 2 ml of dichloromethane was added. The mixture, protected from moisture, was stirred at room temperature (25° C.) overnight. The resulting solution was evaporated to a syrup. The syrup was dissolved in dichloromethane and the solution was added to stirred ice. The mixture was stirred for 1 hour during which time it warmed to room temperature. The dichloromethane solution was separated and washed (X4) with water and dried (MgSO$_4$). Evaporation gave a syrup which was subjected to an oil pump vacuum for half an hour. The syrup was dissolved in ether and 2,6-dimethylpiperidine was added to approximate neutrality (pH 9 with pH paper). The crude titled product [2.36 g (81%), mp 138°–140° C.] crystallized readily. Recrystallization (methanol-ether) with decolorization (Nuchar C-190N) gave pure product, mp 141°–143° C.

Analysis for: C$_9$H$_8$ClNO$_4$ C$_7$H$_{15}$N: Calculated: C, 56.06; H, 6.76; Cl, 10.34; N, 8.17. Found: C, 55.90; H, 6.72; Cl, 10.32; N, 8.28.

EXAMPLE 9

2,3-Dihydro-1H-indole-2-carboxylic acid from α-chloro-2-nitrobenzenepropanoic acid 2,6-dimethylpiperidine salt using aqueous hydrazine in the presence of sponge nickel To a magnetically stirred suspension of α-chloro-2-nitrobenzenepropanoic 2,6-dimethylpiperidine salt (1.714 g, 5.0 mmol) and Raney nickel (0.25 g, Davison No. 28) in water (7 ml) under an atmosphere of nitrogen was added dropwise hydrazine hydrate (1.5 ml, 55.2 mmol) over the course of 1 hour. The temperature of the reaction was allowed to rise to between 30° and 35° C. during this period. (Waterbath cooling was used when necessary). The starting material gradually dissolved during this period. Stirring was continued for a further 2.5 hours. The mixture was filtered through Celite and the purple filtrate was cooled in ice, magnetically stirred, and acidified to pH 2 (pH paper) with concentrated hydrochloric acid. A layer of ether was added to dissolve the initially precipitated impurities. The titled product then crystallized readily. Collection on a filter, followed by consecutive washings with ether, two small aliquots of ice-cold water and ether gave 0.32 g (39%) of the title product, mp 147°–149° C.

Analysis for: $C_9H_9NO_2 \cdot 0.2H_2O$: Calculated: C, 64.82; H, 5.68; N, 8.40. Found: C, 64.89; H, 5.47; N, 8.60.

IR, $^1H$ NMR and mass spectral data were consistent for the above structure.

EXAMPLE 10

α-Chloro-2-nitrobenzenepropanoic Acid

To a magnetically stirred N,N-dimethylformamide (20 ml, 258.5 mmol) cooled in ice was added slowly dropwise thionyl chloride (30 ml, 411.2 mmol). To the resulting cold Vilsmeier reagent was added dichloromethane (100 ml), α-hydroxy-2-nitrobenzenepropanoic acid (20.0 g, 94.7 mmol) and a further 50 mL of dichloromethane as a rinse. The mixture, protected from extraneous moisture, was stirred at room temperature until solution was achieved and the solution was left at room temperature (25° C.) overnight. The solution was poured onto stirred ice and the mixture stirred for 1 hour during which time it warmed to room temperature. The dichloromethane layer was separated, washed thrice with water, dried (MgSO₄) and evaporated to a syrup. The syrup was concentrated further at 40° C. under oil pump vacuum to remove traces of N,N-dimethylformamide. The resulting syrup was stirred magnetically with water while while cooling in ice. The resulting solid was ground in a mortar and collected on a filter. The solid was then stirred magnetically with water, collected on a filter and washed with water. Drying under vacuum over phosphorus pentoxide at room temperature provided 19.60 g (90%) of titled product, mp 107°–109° C.

Analysis for: $C_9H_8ClNO_4$: Calculated: C, 47.08; H, 3.51; Cl, 15.44; N, 6.10. Found: C, 47.29; H, 3.51; Cl, 15.06; N, 6.20.

Spectral data were as previously described.

EXAMPLE 11

Conversion of Crystalline α-Chloro-2-nitrobenzenepropanoic Acid into its 2,6-dimethylpiperidine salt Crystalline α-chloro-2-nitrobenzenepropanoic acid (19.51 g) was dissolved in ether (100–150 ml) and the solution filtered through celite. To the filtrate was added 2,6-dimethylpiperidine until pH 9 (pH paper). Crude product [28.66 g, (98%), mp=138°–140° C.] crystallized readily. Recrystallization with decolorization (Nuchar C-190N) from methanol-ether gave pure product, mp=141°–143° C.

Analysis for: $C_9H_8ClNO_4 \cdot C_7H_{15}N$: Calculated: C, 56.06; H, 6.76; Cl, 10.34; N, 8.17. Found: C, 56.29; H, 6.75; Cl, 10.29; N, 8.44.

What is claimed is:

1. A process for producing an indoline-2-carboxylic acid of the formula:

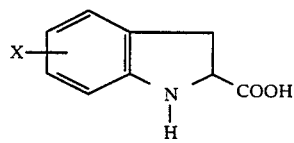

wherein X is hydrogen, chlorine, bromine, $C_{1-4}$ alkyl or $C_{1-4}$ alkoxy, which comprises (a) reducing the nitro group of an α-chloro-2-nitrobenzenepropanoic acid of the formula:

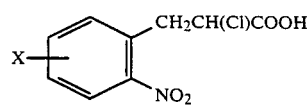

and (b) cyclizing the resulting α-chloro-2-aminobenzenepropanoic acid in aqueous base.

2. A process according to claim 1 in which steps a and b are done in combination.

3. A process according to claim 1 in which X is hydrogen.

* * * * *